United States Patent [19]
Bayer et al.

[11] Patent Number: 5,728,554
[45] Date of Patent: Mar. 17, 1998

[54] IMPROVED ENZYMATIC SYNTHESIS OF GLYCOSIDIC LINKAGES

[75] Inventors: Robert J. Bayer, San Diego; Shawn DeFrees, San Marcos; Murray Ratcliffe, Carlsbad, all of Calif.

[73] Assignee: Cytel Corporation, San Diego, Calif.

[21] Appl. No.: 419,669

[22] Filed: Apr. 11, 1995

[51] Int. Cl.$^6$ .................. C12P 19/18; C12P 19/12; C12P 19/04; C12P 19/00
[52] U.S. Cl. .................. 435/97; 435/72; 435/74; 435/84; 435/100; 435/101
[58] Field of Search .................. 435/97, 72, 74, 435/84, 100, 101

[56] References Cited

U.S. PATENT DOCUMENTS

| | | | |
|---|---|---|---|
| 5,164,374 | 11/1992 | Rademacher | 514/23 |
| 5,278,299 | 1/1994 | Wong | 536/53 |
| 5,288,637 | 2/1994 | Roth | 435/288 |
| 5,352,670 | 10/1994 | Venot | 514/54 |
| 5,374,541 | 12/1994 | Wong et al. | 435/74 |
| 5,374,655 | 12/1994 | Kashem et al. | 514/540 |

FOREIGN PATENT DOCUMENTS

| | | |
|---|---|---|
| WO 92/16640 | 10/1992 | WIPO. |
| WO 9425615 A | 10/1994 | WIPO. |
| 9426760 | 11/1994 | WIPO. |

OTHER PUBLICATIONS

Ichikawa et al., J. Am. Chem. Soc. 113(16):6300–6302 (1991).
David et al., Pure & Applied Chem 59(11):1501–1508 (1987).
Carlson, Don M., et al. (1973) "Synthesis of Sialyl Lactose By A Sialyltransferase From Rat Mammary Gland", *The Journal of Biological Chemistry*, 248(160) :5742–5750.
Ito, et al. (1993) *Pure Appl. Chem.* 65:753.
Van den Eijnden, et al. (1981) *J. Biol. Chem.*, 256:3159.
Weinstein, et al. (1982) *J. Biol. Chem.*, 257:13845.
Wen et al (1992) *J. Biol. Chem.*, 267:21011.
Rearick, et al. (1979) *J. Biol. Chem.*, 254:4444.
Gillespie, et al. (1992) *J. Biol. Chem.*, 267:21004.
Kurosawa, et al. (1994) *Eur. J. Biochem.*, 219:375–381.
Gross, et al. (1987) *Eur. J. Biochem.*, 168:595.
Vijay, et al. (1975) *J. Biol. Chem.*, 250(1) :164.
Zapata, et al. (1989) *J. Biol. Chem.*, 264(25) :14769.
Higa, et al. (1985) *J. Biol. Chem.*, 260(15) :8838.
Vann, et al. (1987) *J. Biol. Chem.*, 262:17556.
Shames, et al. (1991) *Glycobiology*, 1:187.
Nunez, H.A., et al. (1976) "The Metal Ion Catalyzed Decomposition of Nucleoside Diphosphate Sugars", *Biochemistry*, 15(17) :3843–3847.
Wong, Chi–Huey, et al. (1992) "Regeneration of Sugar Nucleotide for Enzymatic Oligosaccharide Synthesis: Use of Gas–1–Phopsphate Uridyltransferase in the Regeneration of UDP–Galactose, UDP–2–Deoxygalactose, and UDP–Talactosamine", *J. Org. Chem.*, 57(16) :4343–4344.
Kurosawa, et al. (1993) *J. Biol. Chem.*, 268:26273–78.
Livingston, et al. (1993) *J. Biol. Chem.*, 268:11504.
Simon, et al. (1988) *J. Am. Chem. Soc.*, 110:7159.
Dabkowski, et al. (1993) *Transplant Proc.*, 25:2921.
Yamamoto, et al. (1990) *Nature*, 345:229–233.
Auge, et al. (1990) *Carbohydrate Research* 200:257–268.
Auge, et al. (1986) *Carbohydrate Research* 151:147–156.
Ichikawa, et al. (1991) *J. Am. Chem. Soc.*, 113:4698–4700.
DeLuca, et al. (1995) *J. Am. Chem. Soc.*, 117:5869–5870.

*Primary Examiner*—Leon B. Lankford, Jr.
*Assistant Examiner*—Francisco C. Prats
*Attorney, Agent, or Firm*—Townsend and Townsend and Crew LLP

[57] ABSTRACT

The present invention provides improved methods for the formation of glycosidic linkages. These methods are useful for the preparation of compounds of formula:

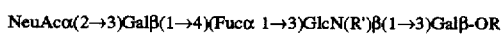

NeuAcα(2→3)Galβ(1→4)(Fucα 1→3)GlcN(R')β(1→3)Galβ-OR

28 Claims, 4 Drawing Sheets

IMPROVED ENZYMATIC SYNTHESIS OF GLYCOSIDIC LINKAGES

CROSS-REFERENCE TO RELATED APPLICATIONS

This disclosure is related to copending application, Ser. No. 08/419,659, filed Apr. 11, 1995.

FIELD OF THE INVENTION

The present invention relates to the synthesis of oligosaccharides. In particular, it relates to improved enzymatic syntheses of such compounds in a single vessel using readily available starting materials.

BACKGROUND OF THE INVENTION

Increased understanding of the role of carbohydrates as recognition elements on the surface of cells has led to increased interest in the production of carbohydrate molecules of defined structure. For instance, compounds comprising the sialyl Lewis ligands, sialyl Lewis$^x$ and sialyl Lewis$^a$ are present in leukocyte and non-leukocyte cell lines that bind to receptors such as the ELAM-1 and GMP 140 receptors. Polley et al., *Proc. Natl. Acad. Sci., USA*, 88:6224 (1991) and Phillips et al., *Science*, 250:1130 (1990), see, also, U.S. Ser. No. 08/063,181.

Because of interest in making desired carbohydrate structures, glycosyltransferases and their role in enzyme-catalyzed synthesis of carbohydrates are presently being extensively studied. These enzymes exhibit high specificity and are useful in forming carbohydrate structures of defined sequence. Consequently, glycosyltransferases are increasingly used as enzymatic catalysts in synthesis of a number of carbohydrates used for therapeutic and other purposes.

In the application of enzymes to the field of synthetic carbohydrate chemistry, the use of glycosyltransferases for enzymatic synthesis of carbohydrate offers advantages over chemical methods due to the virtually complete stereoselectivity and linkage specificity offered by the enzymes (Ito et al., *Pure Appl. Chem.*, 65:753 (1993) U.S. Pat. Nos. 5,352, 670, and 5,374,541).

Improved methods for enzymatic synthesis of carbohydrate compounds would advance the production of a number of beneficial compounds. The present invention fulfills these and other needs.

SUMMARY OF THE INVENTION

The present invention provides improved methods for the formation of glycosidic linkages. In particular, the methods comprise (a) providing a reaction medium comprising at least one glycosyl transferase, a donor substrate, an acceptor sugar and a divalent metal cation; and (b) supplementing the concentration of the divalent cation to maintain the concentration in the reaction medium between about 2 mM and about 75 mM for a period of time sufficient to form the glycosidic linkage. Supplementing the divalent metal cation can be carried out either periodically or continuously.

The divalent metal cation used in the methods can be $Mn^{++}$, $Mg^{++}$, $Ca^{++}$, $Co^{++}$, $Cu^{++}$, $Zn^{++}$ or combinations thereof. Typically the cation is $Mn^{++}$. The glycosyltransferase can be a sialyltransferase, a galactosyltransferase, a fucosyltransferase, a glucosyltransferase, or an N-acetylglucosaminyltransferase.

The invention also provides methods of preparing carbohydrate compounds capable of inhibiting binding of ELAm-1 to its ligand. These compounds are particularly useful in various therapeutic and diagnostic applications.

BRIEF DESCRIPTION OF THE DRAWINGS

FIG. 1 provides a schematic illustration of the preparation of a compound of formula: NeuAcα(2→3)Galβ(1→4)(Fucα 1→3)GlcNAcβ(1→3)Galβ-OR.

DETAILED DESCRIPTION OF THE INVENTION

The present invention provides methods for the formation of a glycosidic linkage which takes place in a reaction medium comprising at least one glycosyl transferase, a donor substrate, an acceptor sugar and a divalent metal cation. The methods rely on the use of a glycosyl transferase to catalyze the addition of a saccharide to a substrate saccharide. The addition takes place at the non-reducing end of an oligosaccharide or carbohydrate moiety on a biomolecule. Biomolecules as defined here include but are not limited to biologically significant molecules such as proteins (e.g., glycoproteins), and lipids (e.g., glycolipids, phospholipids, sphingolipids and gangliosides). In the present methods, the divalent metal ion concentration is supplemented periodically throughout the formation of the glycosidic linkage to maintain the concentration of the metal cation in the reaction medium between about 2 mM and about 75 mM.

The following abbreviations are used herein:

Ara=arabinosyl;

Fru=fructosyl;

Fuc=fucosyl;

Gal=galactosyl;

GalNAc=N-acetylgalacto;

Glc=glucosyl;

GlcNAc=N-acetylgluco;

Man=mannosyl; and

NeuAc=sialyl (N-acetylneuraminyl).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3) Each saccharide is a pyranose.

EMBODIMENTS OF THE INVENTION

Figure 3:
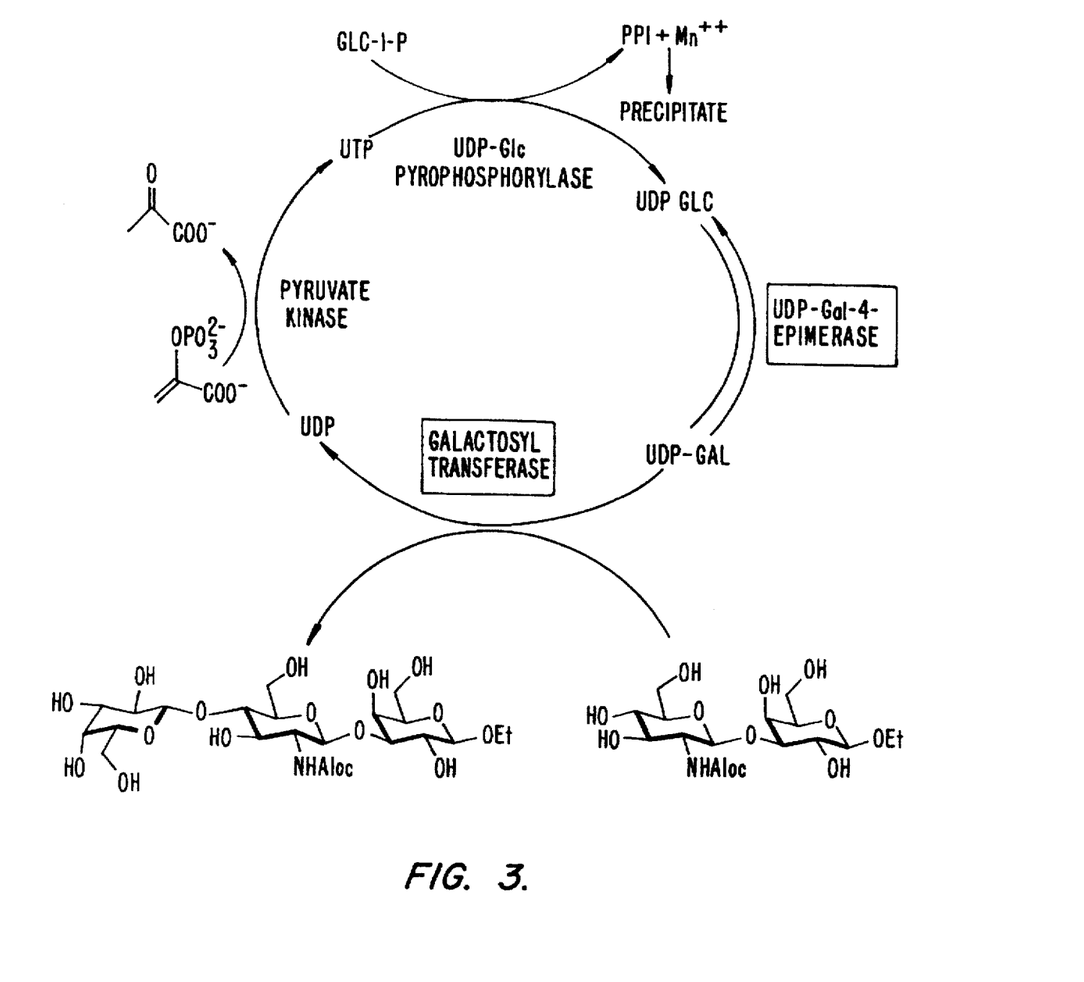
FIG. 3 illustrates a galactosyl transferase cycle of the invention.
Figure 4:
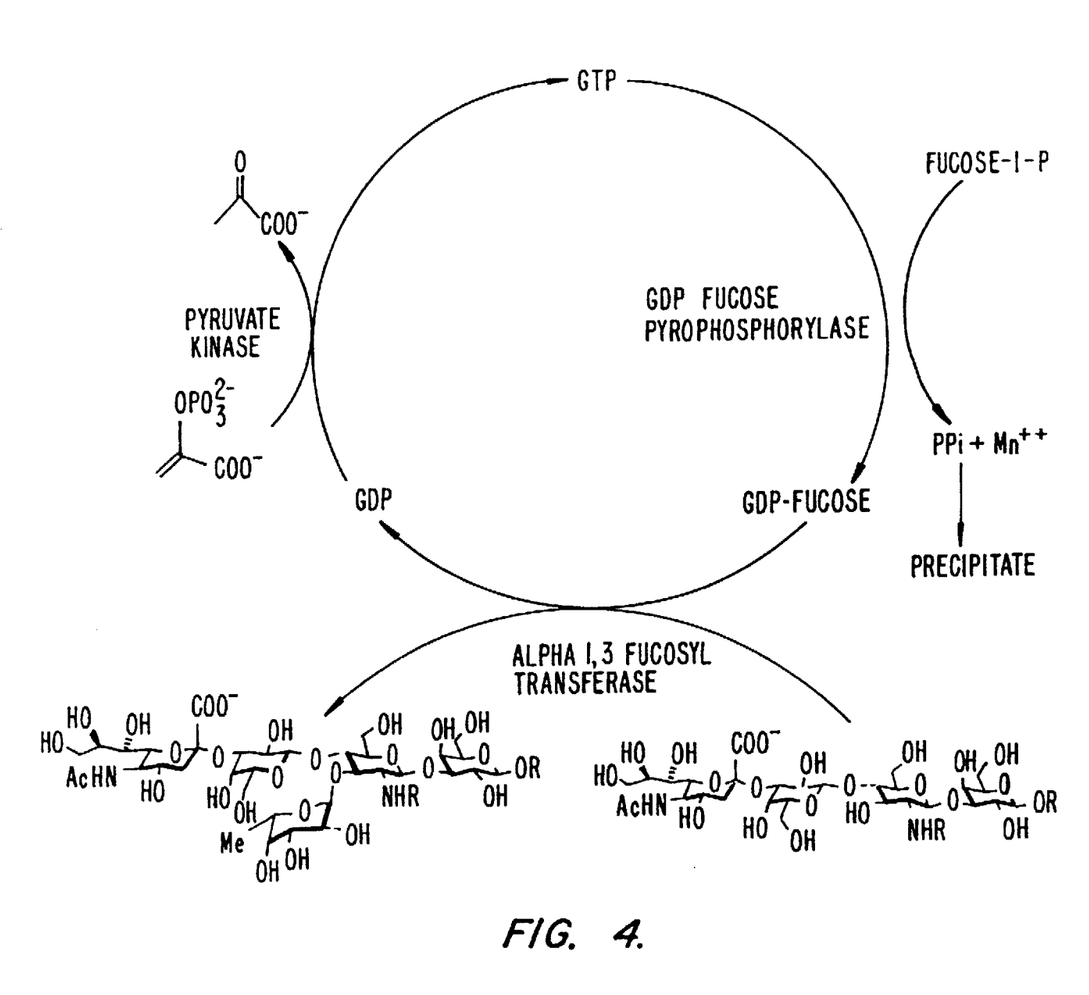
FIG. 4 illustrates a fucosyl transferase cycle.

A number of glycosyl transferase cycles (for example, the sialyltransferase cycle depicted in FIG. 2, the galactosyltransferase cycle depicted in FIG. 3 and the fucosyltransferase cycle depicted in FIG. 4) are useful for the preparation of oligosaccharides. See, U.S. Pat. No. 5,374,541 and WO 9425615 A. These enzyme cycles produce one mole of inorganic pyrophosphate for each mole of product formed and are typically carried out in the presence of a divalent metal ion. The metal ion is a cofactor for at least one of the enzymes in each of the cycles. However, the combination of pyrophosphate and some divalent metal cations produces a complex of particularly low solubility. This, in turn, results in reduced amounts of metal ions present in solution and a corresponding decrease in the overall turnover rates for those enzymes which require the metal ion cofactors. One potential solution to this problem involves beginning with large concentrations of metal ion cofactors. However, the use of large concentrations of metal ion cofactors has proven detrimental to both the galactosyltransferase and sialyltransferase cycles. Alternatively, others have incorporated inorganic pyrophosphatase into the reaction medium in an attempt to drive the reaction cycles to completion by removal of pyrophosphate. Nevertheless, complexes of limited solubility are formed between the orthophosphate produced by inorganic pyrophosphatase and the metal ion cofactor, with the effective reduction in metal ion concentrations. An alternative solution to the problem of metal ion depletion in these cycles is to supplement to metal ion concentrations either continually or periodically throughtout the cyclic process. Thus, the present invention will find application in the cyclic glycosyl transferase processes described herein, and any other process for the formation of glycosidic linkages in which the nucleoside portion of a donor substrate or donor sugar is either recycled or can be represented as part of a recycling process similar to those shown in FIGS. 2–4.

Thus, the present invention provides in one aspect a method for the enzyme-mediated formation of a glycosidic linkage. In this method a medium (typically an aqueous solution) is provided which contains at least one glycosyl transferase, a donor substrate, an acceptor sugar and a divalent metal cation. The concentration of the divalent metal cation in the reaction medium is maintained between about 2 mM and about 75 mM, preferably between about 5 mM and about 50 mM and more preferably between about 5 and about 30 mM.

By periodically or continuously monitoring the metal ion concentration in the reaction medium and supplementing the medium by additional amounts of divalent metal ions, the reaction cycles can be driven to completion within a suitable timeframe. Additionally, if more than one glycosyltransferase is used, consecutive cycles can be carried out in the same reaction vessel without isolation of the intermediate product. Moreover, by removing the inhibitory pyrophosphate, the reaction cycles can be run at substantially higher substrate (acceptor) concentration. Preferred divalent metal ions for use in the present invention include $Mn^{++}$, $Mg^{++}$, $Co^{++}$, $Ca^{++}$, $Zn^{++}$ and combination thereof. More preferably, the divalent metal ion is $Mn^{++}$.

In one group of embodiments, the glycosyltransferase is a sialyltransferase. When a sialyltransferase is used, the reaction medium will preferably contain, in addition to the sialyltransferase, donor substrate, acceptor sugar and divalent metal cation, (i) a catalytic amount of a CMP-sialic acid synthetase, (ii) a sialic acid, and (iii) a CMP-sialic acid recycling system comprising at least 2 moles of phosphate donor per each mole of sialic acid, and catalytic amounts of a nucleoside triphosphate, a kinase capable of transferring phosphate from the phosphate donor to nucleoside diphosphates, and a nucleoside monophosphate kinase capable of transferring the terminal phosphate from a nucleoside triphosphate to CMP.

An α(2,3)sialyltransferase, often referred to as the sialyltransferase, is the principal enzyme utilized herein in the production of sialyl lactose. This enzyme transfers sialic acid to a Gal with the formation of an α-linkage between the two saccharides. Bonding (linkage) between the saccharides is between the 2-position of NeuAc and the 3-position of Gal.

An exemplary α(2,3)sialyltransferase referred to as α(2,3)sialtransferase (EC 2.4.99.6) transfers sialic acid to the non-reducing terminal Gal of a Galβ1→3Glc disaccharide or glycoside. See, Van den Eijnden et al., *J. Biol. Chem.*, 256:3159 (1981), Weinstein et al., *J. Biol. Chem.*, 257:13845 (1982) and Wen et al., *J. Biol. Chem.*, 267:21011 (1992). Another exemplary α(2,3)sialyltransferase (EC 2.4.99.4) transfers sialic acid to the non-reducing terminal Gal of the disaccharide or glycoside. See, Rearick et al., *J. Biol. Chem.*, 254:4444 (1979) and Gillespie et al., *J. Biol. Chem.*, 267:21004 (1992).

Further exemplary enzymes inlcude Gal-β-1,4-GlcNAc α(2,6) sialyltransferases (see, Kurosawa et al. *Eur. J. Biochem.* 219:375–381 (1994), Kurosawa et al. J. Biol. Chem. 269:1402 (1994)) and GM3 synthase (*J. Biol Chem.* 268:26273–78 (1993)) and α(2,8) sialyltransferase (Livingston et al. *J. Biol. Chem.* 268:11504 (1993)).

A second principle enzyme used in the present methods is CMP-sialic acid synthetase. This enzyme is utilized in the CMP-sialic acid regenerating system, discussed in detail hereinafter. CMP-sialic acid synthetase can be isolated and purified from cells and tissues containing the synthetase enzyme by procedures well known in the art. See, for example, Gross et al., *Eur. J. Biochem.*, 168:595 (1987), Vijay et al., *J. Biol. Chem.*, 250(1):164 (1975), Zapata et al., *J. Biol. Chem.*, 264(25):14769 (1989) and Higa et al., *J. Biol. Chem.*, 260(15):8838 (1985). The gene for this enzyme has also been sequenced. See, Vann et al., *J. Biol. Chem.*, 262:17556 (1987). An overexpression of the gene, has also been reported for use in a gram scale synthesis of CMP-NeuAc. See, Shames et al., *Glycobiology*, 1:187 (1991). This enzyme is also commercially available.

A sialic acid is also required. A contemplated sialic acid includes not only sialic acid itself (5-N-acetylneuraminic acid; 5-N-acetylamino-3,5-dideoxy-D-glycero-D-galacto-2-nonulosonic acid; NeuAc, and sometimes also abbreviated AcNeu or NANA), but also 9-substituted sialic acids such as a 9-O-$C_1$-$C_6$ acyl-NeuAc like 9-O-lactyl-NeuAc or 9-O-acetyl-NeuAc, 9-deoxy-9-fluoro-NeuAc and 9-azido-9-deoxy-NeuAc. The synthesis and use of these compounds in a sialylation procedure is disclosed in international application WO 92/16640, published Oct. 1, 1992. Other suitable sialic acids include N-glycolyl neuraminic acid, 5-hydroxyneuraminic acid, 5-CbzNH, 5-CH$_3$OC(O)NH neuraminic acid (Shames et al. *Glycobiol.* 1:187 (1991)), and 5-N-acyl neuraminic acid.

The reaction mixture will also contain an acceptor for the sialyltransferase. Suitable acceptors, include, for example, galactosyl acceptors such as, Galβ1→3GalNAc, lacto-N-tetraose, Galβ1→3GlcNAc, Galβ1→3Ara, Galβ1→6GlcNAc, Galβ1→Glc (lactose), Galβ1→4Glcβ1-OCH$_2$CH$_3$, Galβ1→4Glcβ1-OCH$_2$CH$_2$CH$_3$, Galβ1→4Glcβ1-OCH$_2$C$_6$H$_5$, Galβ1→4GlcNH-acyl, Galβ1→4GlcNAlloc, Galβ1-OCH$_3$, melibiose, raffinose, stachyose and lacto-N-neotetraose. Suitable sialyl acceptors include sialylacα2-OR or sialylacα2→8sialyl-OR, wherein OR is as described below.

Figure 2:
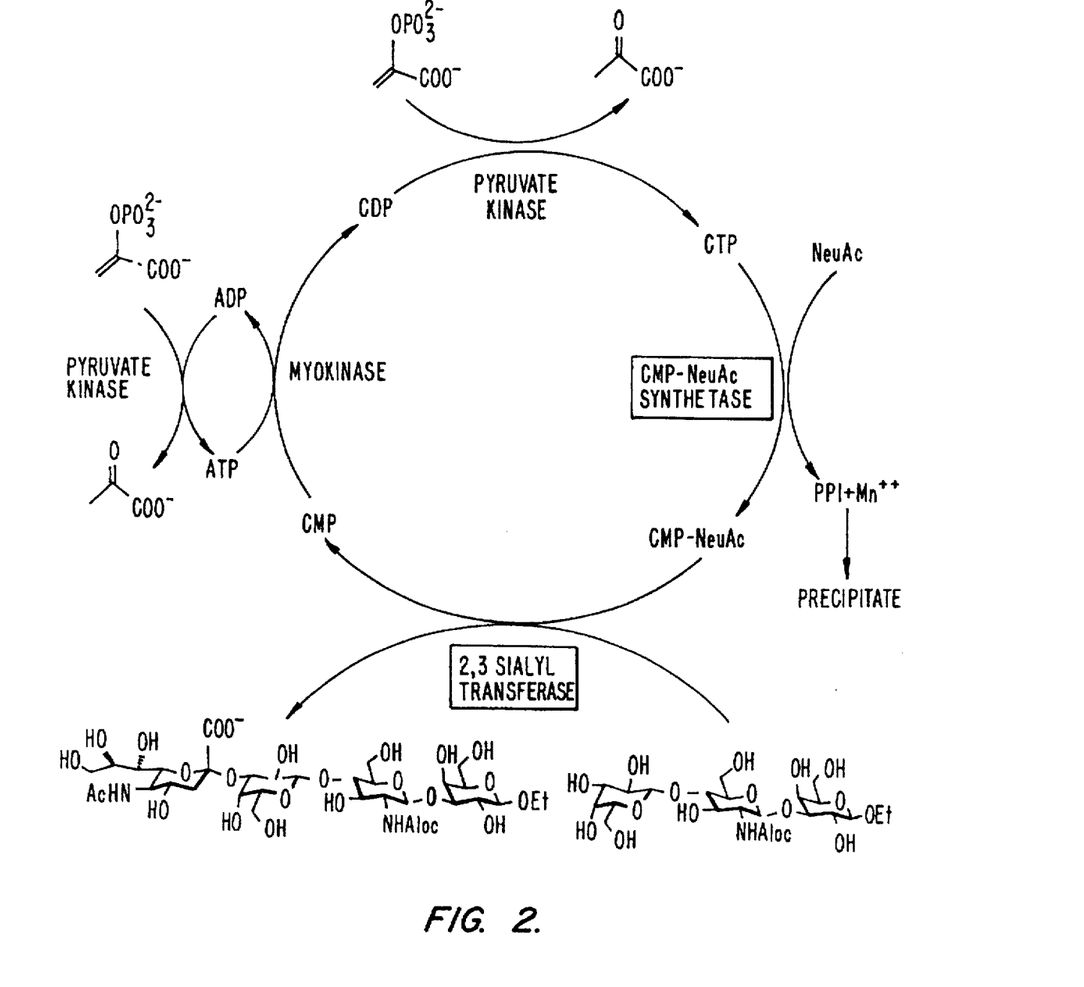
FIG. 2 illustrates a sialyl transferase cycle of the invention.

The CMP-sialic acid recycling system utilizes CMP-sialic acid synthetase as noted previously. As shown in FIG. 2, CMP-sialic acid (shown in FIG. 2 as CMP-NeuAc) reacts with a sialyltransferase acceptor in the presence of a α(2,3)sialyltransferase to form the sialyl lactose.

The CMP-sialic acid regenerating system used in the present invention comprises cytidine monophosphate (CMP), a nucleoside triphosphate (for example adenosine triphosphate (ATP), a phosphate donor (for example, phosphoenolpyruvate or acetyl phosphate), a kinase (for example, pyruvate kinase or acetyl kinase) capable of transferring phosphate from the phosphate donor to nucleoside diphosphates and a nucleoside monophosphate kinase (for example, myokinase) capable of transferring the terminal phosphate from a nucleoside triphosphate to CMP. The previously discussed α(2,3)sialyltransferase and CMP-sialic acid synthetase can also be formally viewed as part of the CMP-sialic acid regenerating system. However, because those two enzymes have already been discussed, they will not be discussed further here.

Nucleoside triphosphates suitable for use in accordance with the CMP-sialic acid regenerating system are adenosine triphosphate (ATP), cytidine triphosphate (CTP), uridine triphosphate (UTP), guanosine triphosphate (GTP), inosine triphosphate (ITP) and thymidine triphosphate (TTP). A preferred nucleoside triphosphate is ATP.

Nucleoside monophosphate kinases are enzymes that catalyze the phosphorylation of nucleoside monophosphates. Nucleoside monophosphate kinase (NMK) or myokinase (MK; EC 2.7.4.3) used in accordance with the CMP-sialic acid regenerating system of the present invention are used to catalyze the phosphorylation of CMP. NMK's are commercially available (Sigma Chem. Co., St. Louis, Mo.; Boehringer Mannheim, Indianapolis, Ind.).

A phosphate donor and a catalytic amount of a kinase that catalyzes the transfer of phosphate from the phosphate donor to an activating nucleotide are also part of the CMP-sialic acid regenerating system. The phosphate donor of the regenerating system is a phosphorylated compound, the phosphate group of which can be used to phosphorylate the nucleoside phosphate. The only limitation on the selection of a phosphate donor is that neither the phosphorylated nor the dephosphorylated forms of the phosphate donor can substantially interfere with any of the reactions involved in the formation of the sialylated acceptor saccharide. Preferred phosphate donors are phosphoenolpyruvate (PEP) and acetyl phosphate. A particularly preferred phosphate donor is PEP.

The selection of a particular kinase for use in accordance with the present invention depends upon the phosphate donor employed. When acetyl phosphate is used as the phosphate donor, the kinase is acetyl kinase. When PEP is used as the phosphate donor, the kinase is pyruvate kinase (PK; EC 2.7.1.40). Other kinases can be employed with other phosphate donors as is well known to those of skill in the art. Kinases are commercially available (Sigma Chem. Co., St. Louis, Mo.; Boehringer Mannheim, Indianapolis, Ind.).

Because of the self-contained and cyclic character of this glycosylation method, once all the reactants and enzymes are present, the reaction continues until the first of the stoichiometric substrates (free NeuAc or PEP) or acceptor is consumed.

Thus, in the sialylation example, CMP is converted to CDP, whose conversion is catalyzed by nucleoside monophosphate kinase or myokinase in the presence of added ATP. ATP is catalytically regenerated from its byproduct, ADP, by pyruvate kinase (PK) in the presence of added phosphoenolpyruvate (PEP). CDP is further converted to CTP, which conversion is catalyzed by PK in the presence of PEP. CTP reacts with sialic acid to form inorganic pyrophosphate (PPi) and CMP-sialic acid, the latter reaction being catalyzed by CMP-sialic acid synthetase. Following sialylation of the α(2,3)sialyltransferase acceptor compound, the released CMP re-enters the regenerating system to reform CDP, CTP and CMP-sialic acid. The formed PPi can be scavenged as discussed below, forming inorganic phosphate (Pi) as a byproduct or the PPi or Pi can be removed from solution via precipitation with added divalent metal cations. Pyruvate is also a byproduct.

The byproduct pyruvate can also be made use of in another reaction in which N-acetylmannosamine (ManNAc) and pyruvate are reacted in the presence of NeuAc aldolase (EC 4.1.3.3) to form sialic acid. Thus, the sialic acid can be replaced by ManNAc and a catalytic amount of NeuAc aldolase. Although NeuAc aldolase also catalyzes the reverse reaction (NeuAc to ManNAc and pyruvate), the produced NeuAc is irreversibly incorporated into the reaction cycle via CMP-NeuAc catalyzed by CMP-sialic acid synthetase. In addition, the starting material, ManNAc, can be made by conversion of GlcNAc using methods known in the art (see, e.g., Simon et al., *J. Am. Chem. Soc.* 110:7159 (1988). The enzymatic synthesis of sialic acid and its 9-substituted derivatives and the use of a resulting sialic acid in a different sialylating reaction scheme is disclosed in International application WO 92/16640, published on Oct. 1, 1992, and incorporated herein by reference.

As used herein, the term "pyrophosphate scavenger" refers to substances that serve to remove inorganic pyrophosphate from a reaction mixture of the present invention. Inorganic pyrophosphate (PPi) is a byproduct of the preparation of CMP-NeuAc. Produced PPi can feed back to inhibit other enzymes such that glycosylation is reduced. However, PPi can be degraded enzymatically or by physical means such as sequestration by a PPi binding substance. For instance, PPi can be removed by hydrolysis using inorganic pyrophosphatase (PPase; EC 3.6.1.1), a commercially available PPi catabolic enzyme (Sigma Chem. Co., St. Louis, Mo.; Boehringer Mannheim, Indianapolis, Ind.), and that or a similar enzyme serves as the pyrophosphate scavenger.

As explained below, the preferred method of removing PPi or Pi from the reaction mixture is to maintain divalent metal cation concentration in the medium. In particular, the cations and the inorganic phosphate produced form a complex of very low solubility. By supplementing the cations which are lost by precipitation with pyrophosphate, the rate of reaction can be maintained. As shown below, when cation concentration is maintained in an optimal range, the sialyl transferase reaction cycle can be driven to completion.

In another group of embodiments, the glycosyltransferase is a galactosyltransferase. When a galactosyltransferase is used, the reaction medium will preferably contain, in addition to the galactosyltransferase, donor substrate, acceptor sugar and divalent metal cation, a donor substrate recycling system comprising at least 1 mole of glucose-1-phosphate per each mole of acceptor sugar, a phosphate donor, a kinase capable of transferring phosphate from the phosphate donor to nucleoside diphosphates, and a pyrophosphorylase capable of forming UDP-glucose from UTP and glucose-1-phosphate and catalytic amounts of UDP and a UDP-galactose-4-epimerase. Exemplary galactosyltransferases include α(1,3) galactosyltransferase (E.C. No. 2.4.1.151, see, e.g., Dabkowski et al., *Transplant Proc.* 25:2921 (1993)

and Yamamoto et al. *Nature* 345:229–233 (1990)) and α(1,4) galactosyltransferase (E.C. No. 2.4.1.38).

In another group of embodiments, the glycosyltransferase is a combination of sialyltransferase and galactosyltransferases. In this group of embodiments, the enzymes and substrates can be combined in an initial reaction mixture, or preferably the enzymes and reagents for a second glycosyltransferase cycle can be added to the reaction medium once the first glycosyltransferase cycle has neared completion. By conducting two glycosyltransferase cycles in sequence in a single vessel, overall yields are improved over procedures in which an intermediate species is isolated. Moreover, cleanup and disposal of extra solvents and by-products is reduced.

In another group of embodiments, the glycosyltransferase is fucosyltransferase. A number of fucosyltransferases are known to those of skill in the art. Briefly, fucosyltransferases include any of those enzymes which transfer L-fucose from GDP-fucose to a hydroxy position of an acceptor sugar. Preferably the acceptor sugar is a GlcNAc in a βGal(1→4)βGlcNAc group in an oligosaccharide glycoside. Suitable fucosyltransferases then include the known βGal(1→3,4)βGlcNAc α(1→3,4)fucosyltransferase (FTIII E.C. No. 2.4.1.65) which is obtained from human milk (see, Palcic, et al., *Carbohydrate Res.* 190:1–11 (1989); Prieels, et al., *J. Biol. Chem.* 256:10456–10463 (1981); and Nunez, et al., *Can. J. Chem.* 59:2086–2095 (1981)) and the βGal(1→4)βGlcNAc α(1→3)fucosyltransferases (FTIV, FTV, FTVI, and FTVII, E.C. No. 2.4.1.65) which are found in human serum. A recombinant form of βGal(1→3,4)βGlcNAc α(1→3,4)fucosyltransferase is also available (see, Dumas, et al., *Bioorg. Med. Letters* 1:425–428 (1991) and Kukowska-Latallo, et al., *Genes and Development* 4:1288–1303 (1990)). Other exemplary fucosyltransferases include α1,2 fucosyltransferase (E.C. No. 2.4.1.69). Enzymatic fucosylation may be carried out by the methods described in Mollicone, et al., *Eur. J. Biochem.* 191:169–176 (1990) or U.S. Pat. No. 5,374,655.

One of skill in the art will understand that other glycosyltransferases can be substituted into similar transferase cycles as have been described in detail for the sialyltransferase. In particular, the glycosyltransferase can also be, for instance, glucosyltransferases, e.g., Alg8 (Stagljov et al., *Proc. Natl. Acad. Sci. USA* 91:5977 (1994)) or Alg5 (Heesen et al. *Eur. J. Biochem.* 224:71 (1994)). Suitable N-acetylgalactosaminyltransferases include α(1,3) N-acetylgalactosaminyltransferase, β(1,4) N-acetylglalactosaminyltransferases (Nagata et al. *J. Biol. Chem.* 267:12082–12089 (1992) and Smith et al. *J. Biol Chem.* 269:15162 (1994)) and polypeptide N-acetylglalactosaminyltransferase (Homa et al. *J. Biol. Chem.* 268:12609 (1993)). Suitable N-acetylglucosaminyltransferases include GnTI (2.4.1.101, Hull et al., *BBRC* 176:608 (1991)), GnTII, and GnTIII (Ihara et al. *J. Biolchem.* 113:692 (1993)), GnTV (Shoreiban et al. *J. Biol. Chem.* 268:15381 (1993)), O-linked N-acetylglucosaminyltransferase (Bierhuizen et al. *Proc. Natl. Acad. Sci. USA* 89:9326 (1992)), N-acetylglucosamine-1-phosphate transferase (Rajput et al. *Biochem J.* 285:985 (1992), and hyaluronan synthase. Suitable mannosyltransferases include α(1,2) mannosyltransferase, α(1,3) mannosyltransferase, β(1,4) mannosyltransferase, Dol-P-Man sythase, OCh1, and Pmt1.

Other suitable glycosyltransferase cycles are described in Ichikawa et al. *JACS* 114:9283 (1992), Wong et al. *J. Org. Chem.* 57: 4343 (1992), and Ichikawa et al. in *Carbohydrates and Carbohydrate Polymers*, Yaltami, ed. (ATL Press, 1993).

For the above glycosyltransferase cycles, the concentrations or amounts of the various reactants used in the processes depend upon numerous factors including reaction conditions such as temperature and pH value, and the choice and amount of acceptor saccharides to be glycosylated. Because the glycosylation process permits regeneration of activating nucleotides, activated donor sugars and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants.

Preferably, the concentrations of activating nucleotides, phosphate donor, the donor sugar and enzymes are selected such that glycosylation proceeds until the acceptor is consumed. The considerations discussed below, while in the context of a sialyltransferase, are generally applicable to other glycosyltransferase cycles.

Each of the enzymes is present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

A reagent which is recycled throughout the process is CMP/CDP/CTP. Thus, one can begin the reaction with any single species or combination of CMP, CDP and CTP. Inasmuch as CMP is the less expensive and most readily available of that group, CMP is typically used to start the reaction, with the amounts discussed before being those for the total amount of the species or combination used.

The above ingredients are combined by admixture in an aqueous reaction medium (solution). That medium has a pH value of about 6 to about 8.5. The medium is devoid of chelators that bind enzyme cofactors such as $Mg^{+2}$ or $Mn^{+2}$. The selection of a medium is based on the ability of the medium to maintain pH value at the desired level. Thus, in some embodiments, the medium is buffered to a pH value of about 7.5, preferably with HEPES. If a buffer is not used, the pH of the medium should be maintained at about 6 to 8.5, preferably about 7.2 to 7.8, by the addition of base. A suitable base is NaOH, preferably 6M NaOH.

The reaction medium may also comprise solubilizing detergents (e.g., Triton or SDS) and organic solvents such as methanol or ethanol, if necessary. In addition, the enzymes are preferably utilized free in solution but can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about zero degrees C. to about 45° C., and more preferably at about 20° C. to about 30° C.

The reaction mixture so formed is maintained for a period of time sufficient for the acceptor to be sialylated to form a desired sialylα2→3βgalactoside (sialoside) product. Some of that product can often be detected after a few hours, with recoverable amounts usually being obtained within 24 hours. It is preferred to optimize the yield of the process, and the maintenance time is usually about 36 to about 240 hours.

The products produced by the above processes can be used without purification. However, it is usually preferred to recover the product. Standard, well known techniques for recovery of glycosylated saccharides such as thin or thick layer chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein. Using such techniques, the saccharides prepared by the above methods of the invention (e.g., sialyl lactose) can be produced at essentially 100% purity by proton NMR and TLC.

In another aspect, the present invention provides methods for the preparation of compounds having the formula:

In this formula, R is a hydrogen, a saccharide, an oligosaccharide or an aglycon group having at least one carbon atom. R' can be either acetyl or allyloxycarbonyl (Alloc).

The term "aglycon group having at least one carbon atom" refers to a group —A—Z, in which A represents an alkylene group of from 1 to 18 carbon atoms optionally substituted with halogen, thiol, hydroxy, oxygen, sulfur, amino, imino, or alkoxy; and Z is hydrogen, —OH, —SH, —NH$_2$, —NHR$^1$, —N(R$^1$)$_2$, —CO$_2$H, —CO$_2$R$^1$, —CONH$_2$, —CONHR$^1$, —CON(R$^1$)$_2$, —CONHNH$_2$, or —OR$^1$ wherein each R$^1$ is independently alkyl of from 1 to 5 carbon atoms. In addition, R can be (CH$_2$)$_n$CH(CH$_2$)$_m$CH$_3$ where n,m,o=1–18; (CH$_2$)$_n$-R$^2$ (in which n=0–18), wherein R$^2$ is a variously substituted aromatic ring, preferably, a phenyl group, being substituted with one or more alkoxy groups, preferably methoxy or O(CH$_2$)$_m$CH$_3$, (in which m=0–18), or a combination thereof.

The steps for these methods include:

(a) galactosylating a compound of the formula GlcNR'β(1→3)Galβ-OR with a galactosyltransferase in the presence of a UDP-galactose under conditions sufficient to form the compound: Galβ(1→4)GlcNR'β(1→3)Galβ-OR;

(b) sialylating the compound formed in (a) with a sialyltransferase in the presence of a CMP derivative of a sialic acid using a α(2,3)sialyltransferase under conditions in which sialic acid is transferred to the non-reducing sugar to form the compound: NeuAcα(2→3)Galβ(1→4)GlcNR'β(1→3)Galβ-OR; and (c) fucosylating the compound formed in (b) to provide the NeuAcα(2→3)Galβ(1→4)(Fucα 1→3)GlcNR'β(1→3)Galβ-OR. Additionally, for the present method, at least one of the galactosylating and sialylating steps are conducted in a reaction medium containing a divalent metal cation and the medium is periodically or continually supplemented with the divalent metal cation to maintain the metal ion concentration between about 2 mM and about 75 mM.

The galactosylating and sialylating steps are carried out enzymatically, preferably under the general conditions described above for the methods of forming glycosidic linkages. Accordingly, the galactosylating step is preferably carried out as part of a galactosyltransferase cycle (see FIG. 3) and the sialylating step is preferably carried out as part of a sialyltransferase cycle (see FIG. 2). Preferred conditons and descriptions of other species and enzymes in each of these cycles has been described. In a preferred embodiment, the galactosylating and sialylating steps are carried out in a single vessel.

The fucosylating step can be carried out either chemically or enzymatically. Enzymatic fucosylation can be carried out by contacting the appropriate oligosaccharide with an α(1→3)fucosyltransferase and a compatible GDP-derivative of L-fucose under conditions wherein the fucose is transferred onto the oligosaccharide. The term "α(1→3) fucosyltransferase" refers to any fucosyltransferase which transfers L-fucose from GDP-fucose to a hydroxy position of a GlcNAc in a βGal(1→4)βGlcNAc group in an oligosaccharide glycoside. Suitable fucosyltransferases have been described above and include the known βGal(1→3,4)βGlcNAc α(1→3,4)fucosyltransferase and the βGal(1→4)βGlcNAc α(1→3)fucosyltransferase.

Suitable conditions, known to those of skill in the art, include the addition of the α(1→3)fucosyltransferase to an appropriate mixture of the oligosaccharide and GDP-fucose in an appropriate buffer such as 0.1M sodium cacodylate in appropriate conditions of pH and temperature such as at a pH of 6.5 to 7.5 and a temperature of from 0° C. to 50° C., preferably between 25° C. and 45° C., more preferably between 35° C. and 40° C., for 12 hours to 4 days. The resulting fucosylated product can be isolated and purified using conventional techniques including membrane filtration, HPLC and gel-, reverse phase-, ion exchange-, or adsorption chromatography.

Alternatively, fucosylation of the oligosaccharide produced in step (b) is carried out chemically according to methods described in U.S. Ser. No. 08/063,181, the disclosure of which is incorporated herein by reference.

In a particularly preferred embodiment, R is ethyl, the fucosylation step is carried out chemically, and the galactosylation and sialylation steps are carried out in a single vessel.

In yet another aspect, the present invention provides methods for the preparation of compounds as described in WO 94/26760. Generally these compounds have the formula:

In this formula, R" is alkyl or acyl from 1–18 carbons, 5,6,7,8 - tetrahydro-2-naphthamido; benzamido; 2-naphthamido; 4-amino benzamido; or 4-nitrobenzamido. R$^2$ may be the same as R as described above or may be Galβ-OR (R is as described above).

In the above descriptions, the terms are generally used according to their standard meanings. The term "alkyl" as used herein means a branched or unbranched, saturated or unsaturated, monovalent or divalent, hydrocarbon radical having from 1 to 20 carbons, including lower alkyls of 1–8 carbons such as methyl, ethyl, n-propyl, butyl, n-hexyl, and the like, cycloalkyls (3–7 carbons), cycloalkylmethyls (4–8 carbons), and arylalkyls.

The term "aryl" refers to a radical derived from an aromatic hydrocarbon by the removal of one atom, e.g., phenyl from benzene. The aromatic hydrocarbon may have more than one unsaturated carbon ring, e.g., naphthyl. The term "alkoxy" refers to alkyl radicals attached to the remainder of the molecule by an oxygen, e.g., ethoxy, methoxy, or n-propoxy. The term "alkylthio" refers to alkyl radicals attached to the remainder of the molecule by a sulfur.

The term of "acyl" refers to a radical derived from an organic acid by the removal of the hydroxyl group. Examples include acetyl, propionyl, oleoyl, myristoyl.

The compounds decribed above can then be used in a variety of applications, e.g., as antigens, diagnostic reagents, or as therapeutics. Thus, the present invention also provides pharmaceutical compositions which can be used in treating a variety of conditions. The pharmaceutical compositions are comprised of oligosaccharides made according to the methods described above.

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985). For a brief review of methods for drug delivery, see, Langer, *Science* 249:1527–1533 (1990).

The pharmaceutical compositions are intended for parenteral, intranasal, topical, oral or local administration, such as by aerosol or transdermally, for prophylactic and/or therapeutic treatment. Commonly, the pharmaceutical compositions are administered parenterally, e.g., intravenously. Thus, the invention provides compositions for parenteral administration which comprise the compound dissolved or suspended in an acceptable carrier, preferably an aqueous carrier, e.g., water, buffered water, saline, PBS and the like. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the oliogosaccharides of the invention can be incorporated into liposomes formed from standard vesicle-forming lipids. A variety of methods are available for preparing liposomes, as described in, e.g., Szoka et al., *Ann. Rev. Biophys. Bioeng.* 9:467 (1980), U.S. Pat. Nos. 4,235,871, 4,501,728 and 4,837,028. The targeting of liposomes using a variety of targeting agents (e.g., the sialyl galactosides of the invention) is well known in the art. (see, e.g., U.S. Pat. Nos. 4,957,773 and 4,603,044).

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid derivatized olgosaccharides of the invention.

Targeting mechanisms generally require that the targeting agents be positioned on the surface of the liposome in such a manner that the target moieties are available for interaction with the target, for example, a cell surface receptor. The carbohydrate of the invention may be incorporated into the lipid molecule before the liposome is formed using methods known to those of skill in the art. Alternatively, the liposome may be fashioned in such a way that a connector portion is first incorporated into the membrane at the time of forming the membrane. The connector portion must have a lipophilic portion which is firmly embedded and anchored in the membrane. It must also have a hydrophilic portion which is chemically available on the aqueous surface of the liposome. The hydrophilic portion is selected so that it will be chemically suitable to form a stable chemical bond with the targeting agent which is added later. Therefore, the connector molecule must have both a lipophilic anchor and a hydrophilic reactive group suitable for reacting with the target agent and holding the target agent in its correct position, extended out from the liposome's surface. In some cases it is possible to attach the target agent to the connector molecule directly, but in most instances it is more suitable to use a third molecule to act as a chemical bridge, thus linking the connector molecule which is in the membrane with the target agent which is extended, three dimensionally, off of the vesicle surface.

The compositions containing the oligosaccharides can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient, but generally range from about 0.5 mg to about 2,000 mg of oligosaccharide per day for a 70 kg patient, with dosages of from about 5 mg to about 200 mg of the compounds per day being more commonly used.

In prophylactic applications, compositions containing the oligosaccharides of the invention are administered to a patient susceptible to or otherwise at risk of a particular disease. Such an amount is defined to be a "prophylactically effective dose." In this use, the precise amounts again depend on the patient's state of health and weight, but generally range from about 0.5 mg to about 1,000 mg per 70 kilogram patient, more commonly from about 5 mg to about 200 mg per 70 kg of body weight.

Single or multiple administrations of the compositions can be carried out with dose levels and pattern being selected by the treating physician. In any event, the pharmaceutical formulations should provide a quantity of the oligosaccharides of this invention sufficient to effectively treat the patient.

The oligosaccharides may also find use as diagnostic reagents. For example, labeled compounds can be used to locate areas of inflammation or tumor metastasis in a patient suspected of having an inflammation. For this use, the compounds can be labeled with appropriate radioisotopes, for example, $^{125}I$, $^{14}C$, or tritium.

The oligosaccharide of the invention can be used as an immunogen for the production of monoclonal or polyclonal antibodies specifically reactive with the compounds of the invention. The multitude of techniques available to those skilled in the art for production and manipulation of various immunoglobulin molecules can be used in the present invention. Antibodies may be produced by a variety of means well known to those of skill in the art.

The production of non-human monoclonal antibodies, e.g., murine, lagomorpha, equine, etc., is well known and may be accomplished by, for example, immunizing the animal with a preparation containing the oligosaccharide of the invention. Antibody-producing cells obtained from the immunized animals are immortalized and screened, or screened first for the production of the desired antibody and then immortalized. For a discussion of general procedures of monoclonal antibody production see Harlow and Lane, *Antibodies, A Laboratory Manual* Cold Spring Harbor Publications, N.Y. (1988).

The following examples are offered solely for the purposes of illustration, and are intended neither to limit nor to define the invention.

EXAMPLES

Figure 1:
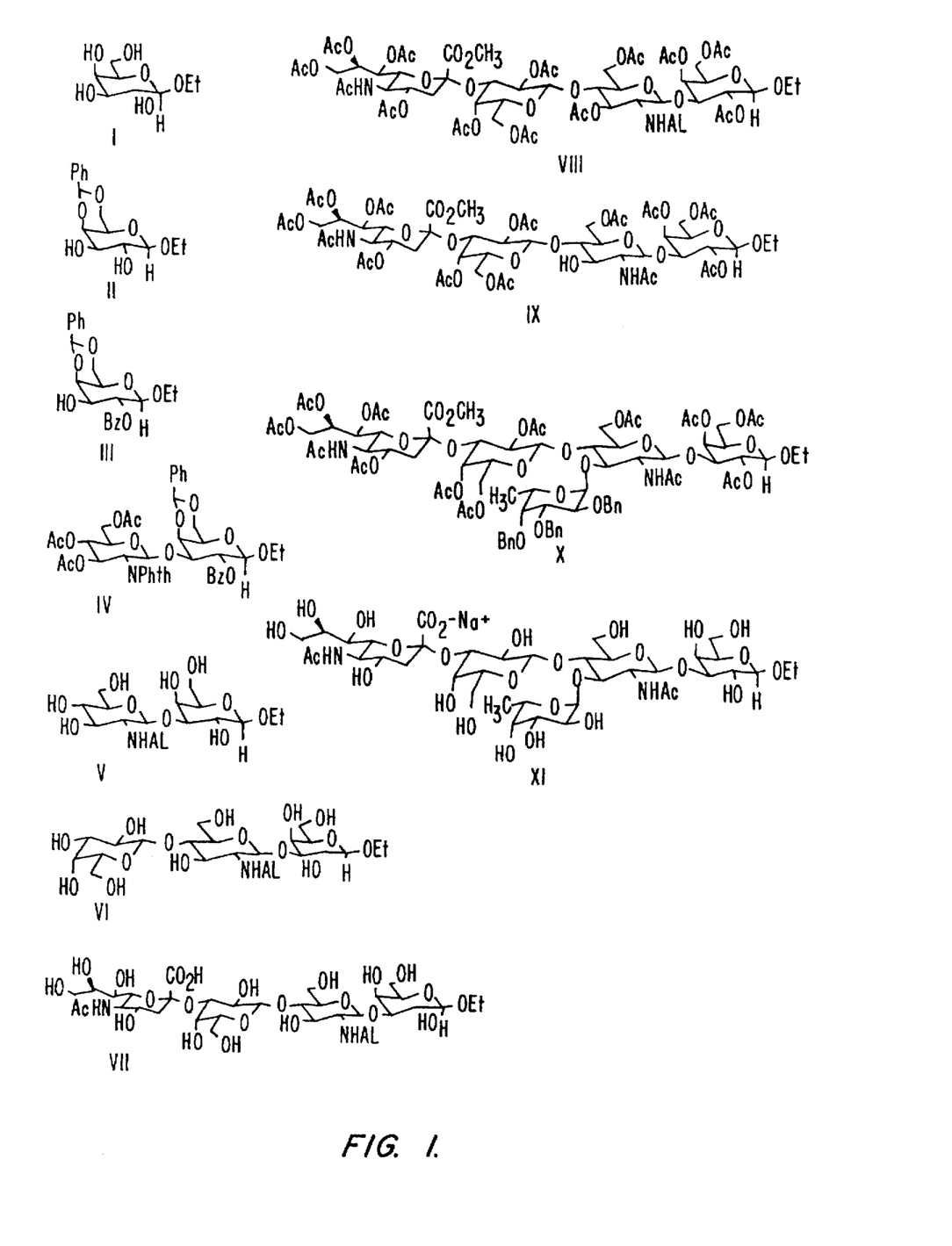

The examples below illustrate the methods of the present invention as applied to the preparation of Ethyl (sodium (5-acetamido-3,5-dideoxy-α-D-glycero-D-galacto-2-nonulopyanosylonate))-(2–3)-O-(β-D-galactopyranosyl)-(1–4)-O-((α-L-fucopyranosyl)-(1–3))-O-(2-acetamido-2-deoxy-β-D-glucopyranosyl)-(1–3)-O-β-D- galactopyranoside. A complete chemical synthesis of this oligosaccharide and the precursors and starting materials has been provided in U.S. Ser. No. 08/063,181, previously incorporated herein by reference. The numbering of the compounds corresponds to the numbering provided in the synthetic scheme of FIG. 1.

EXAMPLE 1

This example illustrates the synthesis of a disaccharide, GlcN(Aloc)(1→3)βGalOEt, used as a substrate in the galactosyl transferase cycle of Example 2. The numbering of the compounds prepared in this example is provided in FIG. 1 which is a schematic for the production of a preferred pentasaccharide.

Preparation of Ethyl β-D-galactopyranoside (I)

A solution of 2,3,4,6-tetra-O-acetyl-galactosyl bromide (2.5 kg) in dichloromethane (4 L) was added at a rate of 20–25 mL/min to a reactor charged with silver carbonate (3.13 kg, 11.4 mol), 4A molecular sieves (2.37 kg), dichloromethane (16 L), and anhydrous ethanol (4.0 L). Agitation was maintained to provide vigorous mixing of the reagents. Two hours after complete addition of the bromide solution, TLC on silica gel developed with hexane:ethyl acetate (1:1) showed no bromide present. At that time the reaction mixture was filtered through a celite pad (1 kg), and the filtrate was evaporated at 30°–35° C. under vacuum to give a brown oil (1.95 kg). This oil was dried under vacuum for 17 hours. $^1$H NMR (CDCL$_3$) δ:5.36 (1H, d, $J_{3,4}$=3.7Hz, H-4), 5.17 (1H, dd, $J_{2,3}$=11.0Hz, H-2), 4.99 (1H, dd,H-3), 4.46 (1H, d, $J_{1,2}$=8.3Hz, H-1), 2.15, 2.05, 2.04, 1.95 (12H, 4s, OAc), 1.21(3H, t, OCH$_2$CH$_3$).

The crude ethyl tetraacetyl galactopyranoside (1.95 kg) was dissolved in anhydrous methanol (11.7 L) and a 25% sodium methoxide in methanol solution (90 mL) was added dropwise. The solution was stirred for one hour at which time TLC on silica gel developed with ethyl acetate:methanol (2:1) showed no starting material to be present. The product had an R$_f$=0.6. The solution was neutralized by the addition of Amberlite IR-120(H$^+$) resin (0.6 kg) with stirring. When the solution pH was between pH 6 and pH 7, the resin was removed by filtration and the filtrate was evaporated under vacuum to afford a pale yellow solid. This solid was dissolved in boiling ethanol (11 L). The resulting solution was allowed to cool to 25° C. and then cooled to 0° C. to give a white precipitate. Filtration of this solid gave ethyl β-D-galactopyranoside (0.851 kg). $^1$H NMR (D$_2$O) δ: 4.38 (1H, d, $J_{1,2}$=8.0Hz, H-1), 3.89 (1H, bd, $J_{3,4}$=3.7Hz, H-4), 1.2 (3H, t, OCH$_2$CH$_3$).

Preparation of Ethyl 4,6-O-benzylidene-β-D-galactopyranoside (II)

Ethyl β-D-galactopyranoside (I) (0.851 kg, 4.09 mol) was charged into a 20 L rotovap flask with toluene sulfonic acid (1.5 g, 7.9 mmol). The evaporator flask was fixed to the evaporator, benzaldehyde dimethyl acetal (1.23 L, 8.18 mol) was added by aspiration and the mixture was tumbled for 4 hours. Between thirty and forty minutes after addition of the acetal, near complete solution was obtained followed rapidly by the appearance of a heavy precipitate. Rotation was continued for 4 hours at which time triethylamine (1.5 mL) was added to neutralize the reaction mixture. A vacuum was applied and the solvent was removed to give a solid mass. Hexane (6 L) was charged into the flask and the mixture tumbled for 0.5 hours. The resulting solid was filtered and washed on the filter with hexane:ethyl ether (1:1, 2 L). The white solid so obtained was dried under vacuum for 17 hours to give pure ethyl 4,6-O-benzylidene-β-D-galactopyranoside (1.0 kg, 3.38 mol) in 83% yield. $^1$H NMR (CDCl$_3$) δ: 7.53 (2H, m, aromatics), 7.37 (3H, m, aromatics), 5.57 (1H, s, CHPh), 4.29 (1H, d, $J_{1,2}$=7.0Hz, H-1), 4.21 (1H, d, $J_{3,4}$=3.27Hz, H-4), 1.29 (3H, t, OCH$_2$CH$_3$).

Preparation of Ethyl 2-O-benzoyl-4,6-O-benzylidene-β-D-galactopyranoside (III)

Ethyl 4,6-O-benzylidene-β-D-galactopyranoside (II) (0.924 kg, 3.12 mol) was put into a 20 liter reactor equipped with an air drive, a pressure equalizing addition funnel with gas inlet, cooling bath, and a gas outlet. Before sealing the flask, dichloromethane (9.3 L) and pyridine (2 L) were added which gave a homogeneous solution. The addition funnel was charged with chloroacetyl chloride (0.388 kg, 3.43 mol, 273 mL) as a 60% solution in dichloromethane. The flask was sealed and a low flow of dry nitrogen was begun. The bath was cooled to −65°±5° C. and the reaction mixture was stirred for 30 minutes. At that time dropwise addition of the acyl chloride solution was begun at a rate of 3–4 mL per minute. After complete addition of this solution the reaction mixture was maintained at −65°±5° C. for an additional 1 hour. At that time benzoyl chloride (0.614 kg, 4.37 mol, 0.507 L) was added to the reaction mixture at a rate of 8–12 mL per minute. The reaction mixture was allowed to warm to room temperature and left for 17 hours. The reaction mixture was filtered to remove precipitated salts and the filtrate was concentrated in vacuo to remove most of the dichloromethane. A small sample was set aside for NMR. $^1$H NMR (CDCl$_3$) δ:5.75 (1H, dd, $J_{2,3}$=0.6Hz, H-2), 5.56 (1H, s, CHPh), 5.25 (1H, dd, $J_{3,4}$=3.44Hz, H-3), 4.69 (1H, d, $J_{1,2}$=8.48Hz, H-1), 4.48 (1H, bd, H-4), 1.15 (3H, t, OCH$_2$CH$_3$). Water (180 mL) was added to the concentrate and the resulting mixture was agitated for two hours at 40° C. At that time the reaction mixture was further concentrated to give a yellow residue that was dissolved in dichloromethane (11 L) and transferred to a 50 liter extractor. The organic solution was successively extracted with ice cold aqueous 0.5N HCl (11 L), aqueous saturated sodium hydrogen carbonate (11 L), cold water (11 L), and the organic layer was dried over anhydrous sodium sulfate (1.0 kg), filtered, and the filtrate evaporated to give a yellow solid which was dried under high vacuum. This reaction was monitored by TLC on silica gel developed with hexane:ethyl acetate (1:1). This solid was dissolved in hot ethanol (9.5 L) which after cooling and filtration gave ethyl 2-O-benzoyl-4,6-O-benzylidene-β-D-galactopyranoside (0.737 kg, 1.85 mol) in 59% yield. $^1$H NMR (CDCl$_3$) δ: 5.59 (1H, s, CHPh), 5.36 (1H, dd, $J_{2,3}$=10.07Hz, H-2), 4.64 (1H, d, $J_{1,2}$=8.21Hz, H-1), 1.15 (3H, t, OCH$_3$CH$_3$).

To confirm that the benzoate is at the C-2 and that C-3 carries a free hydroxyl group, a drop of trichloroacetyl isocyanate was added to the NMR sample and the spectrum was reacquired. This spectrum contained a low field doublet of doublets at δ=5.27 typical of H-3 of galactose which is esterified at C-3. The original filtrate obtained from the reaction mixture contains additional quantities of product.

Preparation of Ethyl 2-O-benzoyl-4,6-O-benzylidene-3-O-(3,4,6-tri-O-acetyl-2-deoxy-2-phthalimido-β-D-glucopyranosyl)-β-D-galactopyranoside (IV)

Ethyl 2-O-benzoyl-4,6-O-benzylidene-β-D-galactopyranoside (III) (1.001 kg, 2.5 mol) was placed in a 20 L reactor that was equipped with a cooling bath, pressure equalizing addition funnel with gas inlet, agitator, and gas outlet. 4A Molecular sieves (1.03 kg), dichloromethane (6.6 L), collidine (0.367 L, 2.77 mol), and, after 15 min stirring, finally silver trifluoromethanesulfonate (0.689 kg, 2.641 mol) were added to the flask under a nitrogen flow. The addition funnel was charged with a solution of 3,4,6-tri-O-acetyl-2-deoxy-2-phthalimido-β-D-glucopyranosyl bromide (1.310 kg, 2.641 mol) dissolved in dichloromethane (2.40 L). The system was sealed and a low purge of nitrogen was maintained and agitation begun, first at room temperature for 1 hr, then cooling (−25° C.) of the reaction vessel was begun and the mixture was stirred at low temperature for another hour. The bromide solution was then added over 1–2 hours. The resulting mixture was allowed to come to ambient temperature and, after 17 hours, the mixture was filtered through a celite pad and the filtrate was washed with aqueous sodium thiosulfate (2M, 3.0 L), water (3 L), hydrochloric acid (1M, 2×2 L), sodium hydrogen carbonate (1M, 3.0 L), and finally water (3 L). The organic layer was dried over anhydrous sodium sulfate, filtered, and evaporated to give a solid. The solid was dissolved in isopropanol:ethyl acetate (1:1, 32 L) at reflux. On cooling to room temperature overnight, a first crop of ethyl 2-O-benzoyl-4,6-O-benzylidene-3-O-(3,4,6-tri-O-acetyl-2-deoxy-2-phthalimido-β-D-glucopyranosyl)-β-D-galactopyranoside was obtained, after filtration and drying. Concentration of the mother liquor (18 L evaporated) and leaving the resulting solution at room temperature overnight gave a second crop of material with acceptable purity. After TLC analysis, the two crops were pooled (1.479 kg, 1.816 mol, 72%). $^1$H NMR (CDCl$_3$) δ: 7.75 (14H, m, aromatics), 5.57 (1H, s, CHPh), 5.38 (1H, dd, J=7.89Hz, J=10.5Hz), 5.16 (1H, t, J=9.99Hz), 4.52 (1H, d, J$_{1,2}$=7.89, H-1), 2.08, 2.01, 1.88 (3H, 3s, OAc), 0.95 (3H, t, OCH$_2$CH$_3$).

Preparation of Ethyl 3-O-(2-N-allyloxycarbonyl-2-amino-2-deoxy-β-D-glucopyranosyl)-β-D-galactopyranoside (V)

To ethyl 2-O-benzoyl-4,6-O-benzylidene-3-O-(3,4,6-tri-O-acetyl-2-deoxy-2-phthalimido-β-D-glucopyranosyl)-β-D-galactopyranoside (IV) (1.017 kg, 1.25 mol) was added 80% acetic acid (10 L). The resulting mixture was heated to 90° C. for 1.25 hours, after which TLC on silica gel developed with ethyl acetate showed the product with R$_f$=0.5–0.6 and complete consumption of the starting material. The solution was evaporated to dryness, and the residue was dissolved in 1:1 ethanol:acetone (6 L) at 70° C. Deionized water (9.0 L) was added to the resulting solution to precipitate the product. The product was filtered and washed with water:acetone 9:1 (6 L) and air dried for 16 hours then dried under vacuum over sodium hydroxide pellets. A second crop was isolated by adding deionized water (4.5 L) to the mother liquor. This material was dried as described above. The yield of the diol was 0.707 kg (81%). $^1$H NMR (CDCl$_3$) δ: 5.67 (1H, dd, J$_{3',4}$=9.07Hz, J$_{2',3}$=11.23Hz, H-3'), 5.57 (1H, d, J$_{1',2}$=9.21Hz, H-1'), 5.32 (1H, dd, J$_{2,3}$=10.08Hz, H-2), 5.12 (1H, t, J$_{4',5'}$=9.07Hz, H-4'), 4.46 (1H, d, J$_{1,2}$=8.64, H-1), 2.14, 2.03, 1.78 (9H, 3s, OAc), 0.98 (3H, t, OCH$_2$CH$_3$).

Ethyl 2-O-benzoyl-3-O-(3,4,6-tri-O-acetyl-2-deoxy-2-phthalimido-β-D-glucopyranosyl)-β-D-galactopyranoside (0.645 kg, 0.882 mol) was dissolved in ethanol (6.5 L) with heating to reflux and stirring. Upon obtaining a clear solution, hydrazine hydrate (0.4 L, 8.25 mol) was added and the mixture heated to reflux, with continued stirring. A precipitate began to appear and after 16 hrs reflux, the reaction was complete as judged be TLC on silica gel developed with ethyl acetate:acetic acid:methanol:water 12:3:3:2. The product had an R$_f$=0.15. The reaction mixture was cooled to ambient temperature, then acetone (5 L) was added, with stirring. Continued stirring gave a homogenous suspension which was filtered to give crude ethyl 3-O-(2-amino-2-deoxy-β-D-glucopyranosyl)-β-D-galactopyranoside, as a white, amorphous powder (0.4 kg) after drying under high vacuum in the presence of phosphorous pentoxide. This crude material was added to a mixture of methanol (5.5 L) and water (0.3 L). Sodium hydrogen carbonate (0.90 kg, 10.7 mol) was added, and the mixture was stirred for 30 min. At that time allyl chloroformate (0.140 L, 1.32 mol) was added, with continued stirring at room temperature. After 1 hour TLC on silica gel developed with ethyl acetate:acetic acid:methanol:water, 12:3:3:2 showed the product with R$_f$=0.6 and the reaction to be complete. The mixture was filtered, and the solid was washed with methanol (0.5 L). The filtrate was evaporated to give a residue. The residue was taken up in water (3.0 L) and extracted with dichloromethane (4.0 L). The aqueous layer was separated and washed with dichloromethane (1.0 L) and concentrated to give a solid. The solid mass was stirred vigorously for 2 hours with acetone:ethyl acetate (1:2, 3 L). The suspension was filtered and the solid was washed with ethyl acetate. Drying under high vacuum in the presence of phosphorous pentoxide for 17 hours gave an off-white powder (0.444 kg). $^1$H NMR (D$_2$O) δ: 5.93 (1H, m, OCH$_2$CH=CH$_2$), 5.35–5.17 (2H, m, OCH$_2$CH=CH$_2$), 4.67 (1H, d, J$_{1',2}$32 8.13Hz, H-1'), 4.35 (1H, d, J$_{1,2}$=8.10Hz, H-1), 4.09 (1H, d, J$_{3,4}$=3.0Hz, H-4), 1.19 (3H, t, OCH$_2$CH$_3$).

EXAMPLE 2

This example illustrates the enzymatic synthesis of βGal (1→4)GlcN(Aloc)(1→3)βGalOEt using the galactosyltransferase cycle with control of manganese ion concentration.

In a polypropylene vessel were combined HEPES (695.3 g, 2.92 mol) and 24 L H$_2$O, and the pH was adjusted to 7.5 with 6M NaOH. Phosphoenolpyruvate monopotassium salt (245.5 g, 1.46 mol), glucose-1-phosphate (470.3 g, 1.31 mol) and bovine serum albumin (29.2 g) were added and the pH was re-adjusted to 7.5 with 6M NaOH. Potassium chloride (152 g, 2.04 mol), sodium azide (14.6 g), uridine diphosphate (15.2 g, 29.3 mmol) and GlcN(Aloc)(1→3) βGalOEt (520 g net, 1.15 mol) were added followed by addition of approximately 1M solutions of MnCl$_2$.4H$_2$O (115.7 g, 0.58 mol) and MgCl$_2$.4H$_2$O (59.3 g, 0.292 mol). Pyruvate kinase (73,000 units), UDP glucose pyrophosphorylase (3000 units), UDP-Gal-4-epimerase (180,000 units), and galactosyl (β1→4) transferase (10,400 units) were added and the volume of the reaction mixture was adjusted to approximately 29 L with H$_2$O. The resulting reaction mixture was maintained at room temperature and monitored daily using thin layer chromatography (tlc) and ion chromatography. Quantitation of manganese and magnesium ions were determined by comparison of ion chromatogram from the reaction mixture with chromatograms from standards containing 30 mM MnCl$_2$ and 30 mM MgCl$_2$.

The manganese ion concentration was measured and supplemented as shown in the table below.

TABLE

| Day | [Mn++] (measured, mM) | Loss of Mn++ (from previous day) | Amount Supplemented (grams, added conc, final concentration) |
|---|---|---|---|
| 1 | 8.7 | 11.3 | 65, 11.3 mM, 20 mM |
| 2 | 3.3 | 16.7 | 115.6, 20 mM, 23.3 mM |
| 3 | 9.8 | 13.5 | 58.4, 10.2 mM, 20 mM |
| 4 | 10.9 | 9.1 | 23.7, 4.1 mM, 15 mM |
| 5 | 7.6 | 7.4 | 42.8, 7.4 mM, 15 mM |
| 6 | 11.3 | 3.7 | none |
| 7 | 8.4 | 2.9 | none |
| 8 | 6.2 | 2.2 | 28.9, 5.0 mM, 11.2 mM |

On day 9, the reaction was essentially complete by TLC (comparison of the product with an authentic sample prepared by synthetic methods described in U.S. Ser. No. 08/063,181). The reaction product was carried on as described in Example 4 below, without purification.

As the results in the table indicate, the depletion of $Mn^{++}$ resulted in additional amounts of $MnCl_2 \cdot 4H_2O$ being added almost daily to maintain the metal ion concentration. Manganese ion is a required cofactor for at least one enzyme in the galactosyltransferase cycle. However, the manganese ion and the inorganic pyrophosphate produced (see FIG. 2) form a complex of very low solubility. Because of this limited solubility, the transferase cycle can continue to proceed, but at reduced reaction rates. By supplementing the manganese ions which are lost by precipitation with pyrophosphate, the rate of reaction can be maintained. Thus, when manganese ion concentration is maintained in an optimal range, the galactosyltransferase reaction cycle can be driven to completion.

EXAMPLE 3

This example illustrates the detrimental effect of concentrations of manganese ion which are initially set at 90 mM.

A 10 mL aliquot of the initial reaction mixture from Example 2 (the mixture prepared at day 0) containing 20 mM $Mn^{++}$ was removed and the manganese ion concentration was adjusted to 90 mM by addition of $MnCl_2 \cdot 4H_2O$. The resulting mixture was monitored daily as described above, however no further additions of manganese ion were made. On day 9, when the reaction from Example 2 was essentially complete (as a result of periodic addition of $MnCl_2 \cdot 4H_2O$), the reaction in the aliquot sample was only about 10–20% complete by TLC.

EXAMPLE 4

This example illustrates the 'one pot' synthesis of αNANA(2→3)βGal(1→4)GlcN(Aloc)(1→3)βGalOEt from the product of the galactosyl transferase cycle using the sialyl transferase cycle with manganese ion control.

Water (16 L) and HEPES (915.8 g, 3.84 mol) were combined in a polypropylene vessel and the pH was adjusted to 7.5 with 6M NaOH. Phosphoenolpyruvate monopotassium salt (511.8 g, 3.05 mol), bovine serum albumin (38.5 g) and sodium azide (19.25 g) were added and the pH was re-adjusted to 7.5 with 6M NaOH. Sialic acid (420 g, 1.36 mol) was added and the pH was re-adjusted to 7.5 with 6M NaOH. Cytidine-5'-monophosphate (43.7 g, 0.135 mol) and adenosine triphosphate (8.1 g, 13.6 mmol) were added and the pH was again adjusted to 7.5 with 6M NaOH. Pyruvate kinase (360,000 units), myokinase (75,000 units), CMP NeuAc synthetase (5000 units), and α2,3 sialyltransferase (2400 units) were added and mixed.

$MnCl_2 \cdot 4H_2O$ (402.1 g, 2.03 mol) was added as an approximately 1M solution to the product solution from Example 2, followed by the addition of the above mix of sialyl transferase cycle components and an additional 20.4 L of water. The resulting reaction mixture was maintained at room temperature and monitored daily using thin layer chromatography (tlc) and ion chromatography. Quantitation of manganese ions was determined by comparison of ion chromatogram from the reaction mixture with chromatograms from standards containing 30 mM $MnCl_2$.

The manganese ion concentration was measured and supplemented as shown in the table below.

TABLE

| Day | [Mn++] (measured, mM) | Loss of Mn++ (from previous day) | Amount Supplemented (grams, added conc, final concentration) |
|---|---|---|---|
| 1 | 23.8 | 10.9 | none |
| 2 | 16.5 | 7.3 | none |
| 3 | 12.7 | 3.8 | 201, 15.0 mM, 27.7 mM |
| 4 | 18.2 | 9.5 | none |
| 5 | 15.0 | 3.2 | none |

The reaction was complete by day 6 as no starting material was detectable by TLC.

EXAMPLE 5

This example illustrates the enzymatic fucosylation of an oligosacharide to produce Ethyl (Ammonium 5-acetamido-3,5-dideoxy-α-D-glycero-D-galacto-2-nonulopyranosylonate)-(2,3)-O-(β-D-galactopyranosyl)-(1,4)-O-(α-L fucopyranosyl-(1,3)-O-(2-acetamido-2-deoxy-β-D-glucopyranosyl)-(1,3)-O-β-D-galactopyranoside.

Ethyl (ammonium 5-acetamido-3,5-dideoxy-α-D-glycero-galacto-2-nonulopyranosylonate)-(2,3)-O-(β-D-galactopyranosyl)-(1,4)-O-(2-acetamido-2-deoxy-β-D-glucopyranosyl)-(1,3)-O-β-D-galactopyranoside (125 mg, 0.141 mmoles) was dissolved into a solution of water (6.2 mL), sodium cacodylate (1M, pH 6.5, 0.72 mL), $MnCl_2$(1M, 0.2 mL) and GDP-β-fucose disodium salt (Sigma, 130 mg, 0.212 mmoles). The alkyline phosphatase (bovine intestine, 32 μL) and fucosyl transferase V (beads, 100 mU) was added and the reaction mixture tipped for 3 days. The reaction was then chromatographed (Biogel P-2, 0.1M $NH_4HCO_3$) to yield after lyophylization 70 mg of the starting material and 76 mg (52%) of XI) as a white solid; $R_f$=0.43 (silica, 30% 1M NH4OAc/iso-propanol).

EXAMPLE 6

This example illustrates the chemical synthesis of NeuAcα(2→3)Galβ(1→4)(Fucα 1→3)GlcNAcβ(1→3)Galβ-OEt, beginning with the tetrasaccharide from Example 4.

Preparation of Ethyl (methyl (5-acetamido-3,5-dideoxy-4,7,8,9-tetra-O-acetyl-α-D-glycero-D-galacto-nonulopyranosylonate))-(2-3)-O-(2,4,6-tri-O-acetyl-β-D-galactopyranosyl)-(1–4)-O-(3,6-di-O-acetyl-2-N-allyloxycarbonyl-2-deoxy-β-D-glucopyranosyl)-(1–3)-O-2,4,6-tri-O-acetyl-β-D-galactopyranside (VIII)

An aqueous solution (40 L) of ethyl (sodium (5-acetamido-3,5-dideoxy-α-D-glycero-D-galacto-nonulopyranosylonate))-(2–3)-O-(β-D-galactopyranosyl)-(1–4)-O-(2-N-allyloxycarbonyl-2-deoxy-β-D- glucopyranosyl)-(1–3)-O-β-D-galactopyranoside (VII) produced from the sequential action of galactosyl and sialyl transferases in the presence of the appropriate cofactors on the disaccharide (V) (0.320 kg) was filtered through paper. The filtrate was run through a membrane with a 3000 molecular weight cut off to remove protein from the desired product. The eluate was concentrated and desalted by running it against a reverse osmosis membrane in a suitable apparatus. The retentate, containing the product, was evaporated to a thick syrup in a 50 L rotavapor. Optionally the retentate can be treated with a chelating resin to remove divalent cations. After filtration the filtrate contained the desired product substantially free of salts and in a high state of purity. The syrup was coevaporated twice with pyridine (2×2 L), then kept under vacuum for 20 hours. The evaporation flask was charged with a solution of N,N-dimethylaminopyridine (20 g) in pyridine (12 L). The rotavapor bath was charged with ice-water mixture, and rotation was continued while acetic anhydride (6 L) was added during a period of 1 hour. Two hours after complete addition more acetic anhydride (2 L) was added and the resulting mixture was left for 20 hours rotating slowly at room temperature. To ensure complete acetylation, more acetic anhydride (1 L) was added and the mixture was rotated for an additional 24 hours. The reaction was checked by TLC (ethyl acetate:hexane:ethanol, 10:10:3). Upon complete reaction vacuum was applied and 14 L of distillate collected.

To the resulting residue, methanol (15 L) was added over a period of 1 hour and the mixture was rotated at room temperature for 20 hours. At this time TLC on silica gel (ethyl acetate:hexane:ethanol, 10:10:3 and dichloromethane:acetone 3:2) showed complete conversion of the lactone to a slower-moving spot which is the methyl ester mono hydroxy compound. The mixture was then concentrated (18 L evaporated) and the mixture was cooled in ice water while acetic anhydride (3 L) was added over a period of 30 minutes. The mixture was left for 20 hours. TLC on silica gel (dichloromethane:acetone 3:2) showed complete acetylation with the product running slightly higher. Methanol (1 L) was added to destroy excess acetic anhydride during which a slight exotherm was noticed. After 1 hour, the mixture was concentrated to a syrup, which was transferred to a 50 L extractor with the aid of ethyl acetate-water mixture (13/13 L). The mixture was agitated vigorously. After phase separation, the lower aqueous layer was drawn off, and the remaining organic layer was filtered through paper. The filtrate was washed with 5% aqueous hydrochloric acid (15 L, the aqueous layer should still be strongly acidic to pH-paper after washing), and aqueous 1M sodium bicarbonate (15 L, the aqueous layer should still be alkaline to pH paper after washing). The organic layer was then transferred to a 20 L container and dried over anhydrous sodium sulfate and filtered. The filtrate was concentrated to a semi-solid residue. This residue was dissolved in dichloromethane (3 L), and applied to a silica gel column (10 kg), packed in dichloromethane. Elution first with dichloromethane (25 L), then with 3:1 dichloromethane:acetone (25 L), and finally with 1:1 dichloromethane:acetone (50 L) gave fractions containing product. Base-line separation was achieved from the disaccharide material, but very little separation was achieved from the traces of slightly faster moving material. The fractions containing product were evaporated, and redissolved in dichloromethane (1.5 L). This solution was slowly added to a vigorously stirred mixture of ethyl ether (7.5 L) and hexane (10 L). The resulting precipitate was filtered and washed with 2:1 ether:hexane, air-dried overnight, then dried in high vacuum for 48 hours. The precipitate (0.61 kg) was shown to be the title compound by NMR. $^1$H NMR contained a small amount of residual solvent (1–5%, weight/weight). $^1$H NMR (CDCl$_3$) δ: 4.67 (d, 1H, H-1"), 4.49 (d, 1H, H-1'), 4.33 (d, 1H, H-1).

Preparation of Ethyl (methyl (5-acetamido-3,5-dideoxy-4,7,8,9-tetra-0-acetyl-α-D-glycero-D-galacto-2-nonulopyanosylonate))-(2,3)-0-(3,4,6-tri-0-acetyl-β-D-galactopyranosyl)-(1,4)-0-(2-acetamido-2-deoxy-6-0-acetyl-β-D-glucopyranosyl)-(1,3)-0-(2,4,6-tri-0-acetyl-β-D-galactopyranoside)
(IX)

To a solution of blocked tetrasaccharide (VIII) (0.532 kg, 0.37 mol) in dry tetrahydrofuran (8 L) was added polymethylhydrosiloxane (PMSH, 46 mL, 0.14 mol). Then Pd(PPH$_3$)$_4$ (14 g, 1.17 mmol) was added and the mixture was degassed under vacuum. The resulting reaction mixture was then stirred at room temperature for 17 hours when TLC (10:10:3, ethyl acetate:hexane: ethanol) showed completion of the reaction. To the reaction mixture was added acetic acid (36 mL, 0.55 mol) and piperidine (60 mL, 0.65 mol). The mixture was stirred at room temperature overnight until TLC (95:5, dichloromethane:methanol) showed completion of the reaction. Evaporation of solvent in vacuo gave a residue which was dissolved in dichloromethane (4 L). This solution was washed successively with water (4 L), 2% aqueous hydrochloric acid (4 L), aqueous sodium hydrogen carbonate (4 L), and finally water (4 L). The organic layer was dried over anhydrous sodium sulfate, filtered and the filtrate evaporated to give a syrup. This syrup was dissolved in methanol (2 L), activated charcoal (200 g) was added and the resulting mixture was heated with stirring to 55° C. for 2 hours. After cooling the mixture was filtered and the filtrate was concentrated to give a residue. This residue was dissolved in dichloromethane (1 L) and added dropwise to a mixture of hexane:ether (1:1, 12 L) to give 0.46 kg of the title compound as a white solid. $^1$H NMR (CD$_3$OD): δ 1.15 (t, 3H, J=7.0Hz, —OCH$_2$CH$_3$); 1.50 (t, 1H, J=12.3Hz, H-3a of NANA); 1.80, 1.91, 1.96, 2.01, 2.02, 2.04, 2.05, 2.07, 2.08, 2.09, 2.10, 2.16, 2.26 (13-Ac); 2.55 (dd, 1H, J=4.6, 12.3Hz, H-3e of NANA); 3.84 (S, 3H, COOCH$_3$).

Preparation of Ethyl (methyl (5-acetamido-3,5-dideoxy-4,7,8,9-tetra-O-acetyl-α-D-glycero-D-galacto-2-nonulopyanosylonate))-2–3)-O-(2,4,6-tri-O-acetyl-β-D-galactopyranosyl)-(1–4)-O-((2,3,4-tri-O-benzyl-α-L-fucopyranosyl)-(1–3))-O-(2-acetamido-6-O-acetyl-2-deoxy-β-D-glucopyranosyl)-(1–3)-O-2,4,6-tri-O-acetyl-β-D-galactopyranoside
(X)

To a solution of the alcohol (IX) (0.118 kg, 0.090 mol) in a mixture of dichloromethane (250 mL) and dimethylformamide (60 mL) was added tetraethylammonium bromide (18.8 g, 0.090 mol). The mixture was then stirred with molecular sieves (4A, 0.250 kg) under nitrogen at room temperature for 6 hours. To the above mixture was added freshly prepared tri-O-benzyl-α-L-fucopyranosyl bromide (0.180 kg, 0.360 mol) in dichloromethane (100 mL). The reaction mixture was then stirred under nitrogen at room temperature for 36 hours until TLC (10:10:3, ethyl acetate:hexane:ethanol) showed completion of the reaction. The reaction mixture was treated with a mixture of methanol (30 mL) and diisopropylethylamine (30 mL) and was stirred at room temperature for 30 minutes. The mixture was diluted with 1 L of dichloromethane and filtered through a bed of celite. The filtrate was washed with aqueous saturated sodium bicarbonate (1.5 L) and water (2 L), and the organic layer dried over magnesium sulfate, filtered, and concentrated to a syrup. This syrup was chromatographed on silica gel (3.5 kg silica gel, 230–400 mesh, ethyl acetate:hexane:ethanol, 5:5:1) to give the title compound (0.110 kg, 73%) as an amorphous solid. $^1$H NMR (CDCl$_3$): δ 1.17 (t, 3H, J=7.2Hz, —OCH$_2$CH$_3$), 1.18 (d, 3H, J=7.0Hz, CH$_3$ of Fuc), 1.60, 1.78, 1.84, 1.99, 2.01, 2.02, 2.04, 2.04, 2.06, 2.06, 2.07, 2.15, 2.19 (13-Ac), 2.55 (dd, 1H, J=4.4, 12.2Hz, H-3e of NANA), 3.82 (s, 3H, COOCH$_3$), 7.4–7.6, (15H, aromatic).

Preparation of Ethyl (sodium (5-3,5-acetamido -3,5-dideoxy-α-D-glycero-D-galacto-2-nonulopyanosylonate))-( 2–3)-O-(β-D-galactopyranosyl)-(1–4)-O-((α-L-fucopyranosyl)-(1–3))-O-(2-acetamido-2-deoxy-β-D-glucopyranosyl)-(1–3)-O-β-D-galactopyranoside To a solution of compound X (105 g, 61 mmol) in acetic acid (900 mL) was added palladium hydroxide on charcoal (20 g, 20% Pd). The reaction mixture was purged two times with hydrogen and then stirred under a hydrogen atmosphere for 8 hours until TLC (90:10, dichloromethane:methanol) showed completion of the reaction. The reaction vessel was purged several times with nitrogen and the reaction mixture was filtered through a bed of celite to remove the catalyst. The celite pad was washed with ethyl acetate several times. Concentration of the filtrate gave the debenzylated product as a white glass (about 97 g). The white glass was dried over high vacuum overnight and was dissolved in ethyl acetate (500 mL). The product triol (79 g, 89%) was precipitated out as white solid with addition of 1 L of a mixture of ether and hexane (8:2). A proton spectrum of the product showed the complete absence of aromatic protons.

To a solution of the triol (79 g, 50 mmol) in methanol (1 L) was added a solution of sodium methoxide (70 mL, 25% w/v). The reaction mixture was stirred at room temperature for 17 hours. Water (100 mL) was added and the mixture was stirred at room temperature for an additional 24 hours until TLC on silica gel (7:2:1, isopropanol:NH$_4$OH:H$_2$O) showed completion of the reaction. To the reaction mixture was added 150 mL of AG-50 H+ ion-exchange resin, which had been thoroughly washed with methanol, and the resulting mixture was stirred at room temperature for 30 minutes. The ion-exchange resin was removed by filtration and filtrate was concentrated to dryness to provide a white glass. The material was dissolved in methanol (300 mL) and filtered through a 0.22 µ nylon membrane. The filtrate was diluted with ethyl ether (300 mL) to give the free pentasaccharide (48 g, 84%) as a white solid. $^1$H NMR (D$_2$O): δ 1.10 (d, 3H, J=6.5Hz, CH$_3$ of Fuc); 1.16 (t, 3H, J=7.0Hz, —OCH$_2$CH$_3$); 1.74 (t, 1H, J=12.2Hz, H-3a of NANA); 1.95, 1.96 (2-Ac); 2.72 (dd, 1H, J=4.4, 12.2Hz, H-3e of NANA); 4.32 (d, 1H, J=8.0Hz, β-anomeric); 4.46 (d, 1H, J=7.4Hz, β-anomeric); 4.65 (d, 1H, J=7.9Hz, β-anomeric); 5.06 (d, 1H, J=4.1Hz, α-anomeric of fucose).

EXAMPLE 7

Alternatively, the pentasaccharide can be made enzymatically starting from compound V of example 1, except that N-allyloxycarbonyl is replaced with N-acetyl. The starting material is enzymatically galactosylated, sialylated and fucosylated using the methods described above.

All publications, patents and patent applications mentioned in this specification are herein incorporated by reference into the specification to the same extent as if each individual publication, patent or patent application was specifically and individually indicated to be incorporated herein by reference.

The above description is illustrative and not restrictive. Many variations of the invention will become apparent to those of skill in the art upon review of this disclosure. Merely by way of example a number of substrates, enzymes, and reaction conditions can be substituted into the glycosyl transferase cycles as part of the present invention without departing from the scope of the invention. The scope of the invention should, therefore, be determined not with reference to the above description, but instead should be determined with reference to the appended claims along with their full scope of equivalents.

What is claimed is:

1. A method for the formation of glycosidic linkages, comprising:
   (a) providing a reaction medium comprising at least one glycosyl transferase, a donor substrate, an acceptor sugar and a divalent metal cation at a concentration of between about 2 mM and about 75 mM; and, after initiation of a glycosidic linkage-forming reaction, as a separate step
   (b) adding sufficient divalent metal cation to said reaction medium to restore a portion of said divalent cation lost during the course of the reaction to thereby achieve or maintain a concentration of said divalent metal cation in said reaction medium between about 2 mM and about 75 mM, and wherein step (b) occurs without interruption of said glycosidic linkage-forming reaction.

2. A method in accordance with claim 1 wherein said divalent metal cation is a member selected from the group consisting of $Mn^{++}$, $Mg^{++}$, $Ca^{++}$, $Co^{++}$, $Zn^{++}$, $Cu^{++}$ and combinations thereof.

3. A method in accordance with claim 1, wherein said adding is periodic.

4. A method in accordance with claim 1, wherein said adding is continuous.

5. A method in accordance with claim 1, wherein said glycosyl transferase is sialyl transferase.

6. A method in accordance with claim 1, wherein said glycosyl transferase is galactosyl transferase.

7. A method in accordance with claim 1, wherein said glycosyl transferase is a combination of sialyl transferase and galactosyl transferase.

8. A method in accordance with claim 1, wherein said glycosyl transferase is fucosyl transferase.

9. A method in accordance with claim 1, wherein said glycosyl transferase is N-acetyl glucosaminyl transferase.

10. A method in accordance with claim 1, wherein said reaction medium further comprises:
   (i) a catalytic amount of a donor sugar synthetase;
   (ii) a donor sugar precursor; and
   (iii) a donor sugar recycling system.

11. A method in accordance with claim 10, wherein said reaction medium comprises:
   (i) a catalytic amount of a CMP-sialic acid synthetase;
   (ii) a sialic acid;
   (iii) a CMP-sialic acid recycling system comprising at least 2 moles of phosphate donor per each mole of sialic acid, and catalytic amounts of a nucleoside triphosphate, cytidine monophosphate, a kinase capable of transferring phosphate from said phosphate donor to a nucleoside diphosphate, and a nucleoside monophosphate kinase capable of transferring the terminal phosphate from a nucleoside triphosphate to CMP; and said acceptor sugar is an acceptor for said sialyltransferase having a galactosyl unit.

12. A method in accordance with claim 11 wherein said sialyltransferase is α(2,3)sialyltransferase.

13. A method in accordance with claim 11 wherein said sialyltransferase is α(2,3)sialyltransferase and said divalent metal cation is $Mn^{++}$.

14. A method in accordance with claim 11 wherein said sialic acid is 5-N-acetylneuraminic acid.

15. A method in accordance with claim 11 wherein said acceptor sugar is a member selected from the group consisting of Galβ(1→4)GlcNAc-OR and Galβ(1→4)GlcN(Alloc)-OR, wherein R is selected from the group consisting of hydrogen, a saccharide, an oligosaccharide and an aglycon group having at least one carbon atom.

16. A method in accordance with claim 15 wherein said sialic acid is 5-N-acetylneuraminic acid.

17. A method in accordance with claim 11 wherein said reaction cycle is conducted in a buffered aqueous medium having a pH value of about 6 to about 8.

18. A method in accordance with claim 6, wherein said galactosyl donor substrate contains a β-galactosyl unit, said galactosyl transferase is present in a catalytic amount and said reaction medium further comprises a donor substrate recycling system comprising at least 1 mole of glucose-1-phosphate per each mole of acceptor sugar; catalytic amounts of UDP, pyruvate kinase, UDP-glucose-pyrophosphorylase and a UDP-galactose-4-epimerase.

19. A method in accordance with claim 18, wherein said acceptor sugar is selected from the group consisting of GlcN(Alloc)(1→3)βGalOEt and GlcNAc(1→3)βGalOEt.

20. A method in accordance with claim 7, wherein said reaction medium further comprises;

(i) a donor substrate recycling system comprising at least 1 mole of glucose-1-phosphate per each mole of acceptor substrate; catalytic amounts of UDP, pyruvate kinase, UDP-glucose-pyrophosphorylase and a UDP-galactose-4-epimerase;

(ii) a catalytic amount of a CMP-sialic acid synthetase;

(iii) a sialic acid;

(iv) a CMP-sialic acid recycling system comprising at least 2 moles of phosphate donor per each mole of sialic acid, and catalytic amounts of a nucleoside triphosphate, cytidine monophosphate, a kinase capable of transferring phosphate from said phosphate donor to a nucleoside diphosphate, and a nucleoside monophosphate kinase capable of transferring the terminal phosphate from a nucleoside triphosphate to CMP.

21. A method in accordance with claim 8, wherein said fucosyltransferase is α(1→3)fucosyltransferase and said donor substrate is a GDP-fucose.

22. A method for the preparation of NeuAcα(2→3)Galβ(1→4)(Fucα 1→3)GlcN(R')β(1→3)Galβ-OR, wherein R is selected from the group consisting of hydrogen, a saccharide, an oligosaccharide and an aglycon group having at least one carbon atom; and R' is selected from the group consisting of acetyl and allyloxycarbonyl; said method comprising:

(a) galactosylating a compound of the formula GlcN(R')β(1→3)Galβ-OR with a galactosyltransferase in the presence of a UDP-galactose under conditions sufficient to form the compound: Galβ(1→4)GlcN(R')β(1→3)Galβ-OR;

(b) sialylating said compound formed in (a) with a sialyltransferase in the presence of a CMP derivative of a sialic acid using a α(2,3)sialyltransferase under conditions wherein sialic acid is transferred to the non-reducing sugar to form the compound: NeuAcα(2→3)Galβ(1→4)GlcN(R')β(1→3)Galβ-OR; and (c) fucosylating said compound formed in (b) to provide said NeuAcα(2→3)Galβ(1→4)(Fucα 1→3)GlcN(R')β(1→3)Galβ-OR;

wherein said galactosylating and sialylating steps are conducted in a reaction medium comprising of from about 2 mM to about 75 mM of a divalent metal cation and wherein said divalent metal cation is added to said medium during one or both of said galactosylating and sialylating steps to restore a portion of the divalent metal cation lost during the course of the reaction and thereby achieve or maintain the concentration of said divalent metal cation between about 2 mM and about 75 mM, and wherein the addition of divalent metal cation occurs without interruption of the galactosylating and sialylating steps.

23. A method in accordance with claim 22, wherein R' is allyloxycarbonyl and said fucosylation step is carried out chemically.

24. A method in accordance with claim 22, wherein said fucosylation step is carried out enzymatically.

25. A method in accordance with claim 22, wherein said galactosylation and said sialylation are carried out in a single vessel.

26. A method in accordance with claim 22, wherein said reaction medium further comprises a UDP-galactose recycling system comprising at least 1 mole of glucose-1-phosphate per each mole of GlcN(R')β(1→3)Galβ-OR and catalytic amounts of UDP, pyruvate kinase, UDP-glucose pyrophosphorylase and a UDP-galactose-4-epimerase.

27. A method in accordance with claim 22, wherein said reaction medium further comprises a CMP-sialic acid recycling system comprising at least 2 moles of phosphate donor per each mole of sialic acid, and catalytic amounts of a nucleoside triphosphate, cytidine monophosphate, a kinase capable of transferring phosphate from said phosphate donor to a nucleoside diphosphate, and a nucleoside monophosphate kinase capable of transferring the terminal phosphate from a nucleoside triphosphate to CMP.

28. A method in accordance with claim 22, wherein R is ethyl; said reaction medium further comprises a UDP-galactose recycling system comprising at least 1 mole of glucose-1-phosphate per each mole of GlcN(R')β(1→3)Galβ-OR and catalytic amounts of UDP, pyruvate kinase, UDP-glucose pyrophosphorylase and a UDP-galactose-4-epimerase and a CMP-sialic acid recycling system comprising at least 2 moles of phosphate donor per each mole of sialic acid, and catalytic amounts of a nucleoside triphosphate, cytidine monophosphate, a kinase capable of transferring phosphate from said phosphate donor to a nucleoside diphosphate, and a nucleoside monophosphate kinase capable of transferring the terminal phosphate from a nucleoside triphosphate to CMP; said fucosylating step is carried out chemically; and steps (a) and (b) are carried out in a single vessel.

* * * * *